(12) United States Patent
Fehre et al.

(10) Patent No.: US 9,162,080 B2
(45) Date of Patent: Oct. 20, 2015

(54) DEVICE FOR X-RAY BRACHYTHERAPY, AND METHOD FOR POSITIONING A PROBE INTRODUCED INTO A BODY FOR X-RAY BRACHYTHERAPY

(75) Inventors: Jens Fehre, Hausen (DE); Bernd Granz, Oberasbach (DE); Markus Lanski, Wasseralfingen (DE); Ralf Nanke, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 1839 days.

(21) Appl. No.: 12/094,891

(22) PCT Filed: Sep. 28, 2006

(86) PCT No.: PCT/EP2006/066849
§ 371 (c)(1),
(2), (4) Date: May 23, 2008

(87) PCT Pub. No.: WO2007/060051
PCT Pub. Date: May 31, 2007

(65) Prior Publication Data
US 2008/0275341 A1 Nov. 6, 2008

(30) Foreign Application Priority Data
Nov. 24, 2005 (DE) .......................... 10 2005 056 080

(51) Int. Cl.
*A61B 8/12* (2006.01)
*A61B 18/00* (2006.01)
(Continued)

(52) U.S. Cl.
CPC ............. *A61N 5/1002* (2013.01); *A61B 8/4416* (2013.01); *A61B 8/5261* (2013.01);
(Continued)

(58) Field of Classification Search
CPC .................. A61N 5/1001; A61N 2005/1025; A61N 5/1027; A61N 5/1002; A61N 5/1048; A61N 5/1049; A61N 2005/1058; A61N 2005/1094; A61M 25/00; A61B 2019/5276; A61B 2019/5425; A61B 2019/5483; A61B 19/5244; A61B 8/4416; A61B 8/5261
USPC ....................................... 600/461; 606/21, 28
See application file for complete search history.

(56) References Cited

U.S. PATENT DOCUMENTS 5,178,148 A * 1/1993 Lacoste et al. ................. 600/439
5,398,690 A * 3/1995 Batten et al. ................... 600/461
(Continued)

FOREIGN PATENT DOCUMENTS

WO WO 2005/092197 10/2005

OTHER PUBLICATIONS

Brochure of Carl Zeiss AG: "Intraoperative Strahlentherapie mit dem INTRABEAM® System von Carl Zeiss" (Sep. 2004).

*Primary Examiner* — Sanjay Cattungal
*Assistant Examiner* — Helene Bor
(74) *Attorney, Agent, or Firm* — Schiff Hardin LLP

(57) ABSTRACT

In a system and method for x-ray brachytherapy, a probe is introduced into the body of a subject, the probe carrying an x-ray source that radiates x-rays into an exposure area outside of the probe within the body of the subject. A number of markers are located in or on the probe, that are detectable in an image generated by an imaging device. The markers are located in or on the probe in a known spatial relation to the exposure area, so that the position of the exposure area can be determined by identifying the markers in the displayed image.

24 Claims, 2 Drawing Sheets

(51) Int. Cl.
*A61N 5/10* (2006.01)
*A61B 19/00* (2006.01)
*A61B 8/00* (2006.01)
*A61B 8/08* (2006.01)

(52) U.S. Cl.
CPC .... *A61B 19/5244* (2013.01); *A61B 2019/5276* (2013.01); *A61B 2019/5425* (2013.01); *A61B 2019/5483* (2013.01); *A61N 5/1049* (2013.01); *A61N 2005/1058* (2013.01); *A61N 2005/1094* (2013.01)

(56) References Cited

U.S. PATENT DOCUMENTS

| | | | |
|---|---|---|---|
| 6,083,166 A * | 7/2000 | Holdaway et al. | 600/439 |
| 6,083,167 A | 7/2000 | Fox et al. | |
| 6,106,517 A * | 8/2000 | Zupkas | 606/20 |
| 6,217,518 B1 * | 4/2001 | Holdaway et al. | 600/443 |
| 6,273,858 B1 * | 8/2001 | Fox et al. | 600/466 |
| 6,475,168 B1 | 11/2002 | Pugsley, Jr. et al. | |
| 6,494,835 B1 * | 12/2002 | Ciezki et al. | 600/439 |
| 6,603,988 B2 * | 8/2003 | Dowlatshahi | 600/407 |
| 7,217,242 B2 * | 5/2007 | Alam et al. | 600/439 |
| 7,278,969 B2 * | 10/2007 | Ueda | 600/463 |
| 8,282,561 B2 * | 10/2012 | Towe | 600/459 |
| 2002/0026188 A1 * | 2/2002 | Balbierz et al. | 606/41 |
| 2002/0115901 A1 | 8/2002 | Tiren | |
| 2005/0000525 A1 * | 1/2005 | Klimberg et al. | 128/898 |
| 2005/0187422 A1 * | 8/2005 | Maschke | 600/3 |
| 2006/0014997 A1 * | 1/2006 | Kindlein et al. | 600/3 |
| 2006/0074303 A1 * | 4/2006 | Chornenky et al. | 600/427 |
| 2006/0100529 A1 * | 5/2006 | Rueckmann et al. | 600/478 |

* cited by examiner

Extracorporeal Ultrasound Applicator

DEVICE FOR X-RAY BRACHYTHERAPY, AND METHOD FOR POSITIONING A PROBE INTRODUCED INTO A BODY FOR X-RAY BRACHYTHERAPY

BACKGROUND OF THE INVENTION

1. Field of the Invention

The invention concerns a device for x-ray brachytherapy as well as a method for positioning of a probe inserted into the inside of a body for x-ray brachytherapy.

2. Description of the Prior Art

X-ray brachytherapy is a therapeutic treatment with x-rays in which the x-ray source is brought very close to the tissue to be treated (for example a tumor or a vessel wall) after the implementation of a endovascular dilatation. In order to able to insert the x-ray source with the aid of a catheter or a probe either without an invasive procedure or with an optimally minimally-invasive procedure inside a body, a miniaturized x-ray source, is required, as is known from U.S. Pat. No. 6,721,392, for example. This is arranged at the distal end of a probe that, for example, is intraoperatively positioned in a tumor or tumor bed (after its extraction), as is explained in detail in the PR information of Carl Zeiss AG, Medical Engineering Innovation by Carl Zeiss AG, "Intraoperative Strahlentherapie mit dem INTRABEAM System von der Carl Zeiss AG" state as of, September 2004, for example.

A miniaturized x-ray source that is arranged in a catheter with which it can be inserted into the body cavities (lumen) in order to irradiate selected tissue zones from the immediate surroundings from there is known from United States Patent Application Publication 2003/0149327 A1. It contains a shielding rotatable around the axis of the catheter in order to radiate the x-rays in a targeted manner at least perpendicular to the axis in a selected solid angle. The surroundings of the catheter can be observed with an optical observation device arranged in a catheter. A light source that exposes only the part of the surface of the hollow space that is also irradiated is used for this purpose.

Given endovascular brachytherapy with a beta or gamma radiator arranged in the tip of a catheter, it is also known from DE 10 2004 008 373 B3 (for example) to arrange an optical observation device in the catheter. For this a brachytherapy catheter is integrated into a unit with an OCT catheter operating on the basis of optical coherence tomography (OCT).

For the therapeutic success it is essential that the x-rays radiating out of the catheter from the x-ray source in an exposure area for most part exclusively strike the tissue (for example the tumor) to be treated in order to ensure an optimally low exposure of the healthy tissue located near this. This requires a precise positioning of the exposure area, i.e. a precise positioning and alignment of the x-ray source or of the solid angle in which the x-rays exit.

SUMMARY OF THE INVENTION

An object of the present invention is provide a device for x-ray brachytherapy with a probe that can be inserted inside a body, with which probe a precise positioning of the exposure area is possible. A further object of the invention is provide a method for positioning a probe inserted inside a body for x-ray brachytherapy.

With regard to the device, the cited object is achieved by a device containing a probe that can be inserted into the inside of a body, the probe at its distal end having an x-ray source that radiates x-ray radiation into an exposure area outside of the probe. Multiple markers is provided that are detectable in an image generated by an imaging device and that are arranged in or at the probe in a known spatial relation to the exposure area. The position of the exposure area in this image can then be concluded from the position of these markers in the image. In other words: the markers indirectly mark the exposure area. This enables a precise positioning of the exposure area, i.e. a precise positioning of the x-ray source and of the solid angle region in which the x-rays generated by the x-ray source are radiated.

As used herein the term "probe" is an instrument that can be introduced into the inside of a body. This can be both a catheter (in the narrower sense) that is inserted into body cavities (transluminal) and a needle-like instrument that can be placed within a tissue zone (percutaneous or interstitial).

An imaging device in the sense of the invention is any device that can be used in medical diagnostics with which two-dimensional or three-dimensional images can be generated that render an area located inside a body. The invention is also not limited to the use of a single imaging device. Rather, imaging systems based on different principles can also be used, in particular imaging devices generating ultrasound images and x-ray images as well as tomographical imaging systems operating on the basis of magnetic resonance. In this case it is advantageous when the markers are detectable in all employed imaging devices.

Moreover, both the navigation and the identification of the spatial position of the exposure area are made easier if the probe and the position of the x-ray source itself are detectable in the image.

If a shielding that can be moved relative to the x-ray source is arranged in the probe to adjust the exposure area, the exposure area can be adjusted more flexibly even given a stationary probe. In this case the markers are advantageously spatially coupled to the shielding. As an alternative to this, in this case the markers can also be arranged stationary on or in the probe when the position of the shielding (i.e. the position of a window or an aperture from which the x-rays exit) is detected relative to the markers with the aid of a sensor or is already known in advance by controlling the movement of the shielding.

In a preferred embodiment of the invention, the device is an imaging device that can be positioned independent of the probe to generate an image rendering at least one part of the exposure area as well as a display device to show the image and to indicate the exposure area in the image. This enables a particularly simple and graphic positioning of the exposure area.

Moreover, if lines of equal dose rating are mixed into the exposure area rendered in the image, the dose rating required at different locations of the exposure area can be adjusted in a targeted manner.

It is particularly advantageous when an optical image of an environment of the probe containing at least one part of the exposure area is generated with the aid of an operation observation device arranged in or on the probe. The correct navigation of the probe is additionally made easier when the exposure area is indicated in the optical image.

In an embodiment of the invention, the imaging device is an ultrasound applicator, in particular an ultrasound probe that can be inserted into a cavity of the body, which ultrasound probe advantageously exhibits an ultrasound transducer arrangement to generate ultrasound images in two slice planes perpendicular to one another.

A device according to the invention is in particular suitable for insertion into a urethra or a ureter and for therapeutic treatment of a prostate, bladder or kidney tumor.

The above object also is achieved in accordance with the present invention by a method for positioning an x-ray brachytherapy probe in the interior of the body of a living subject, including the steps of inserting an x-ray brachytherapy probe into a living subject, the probe having a distal end at which an x-ray source is located, radiating x-rays from the x-ray source into an exposure area in the body of the subject outside of the probe, providing a number of markers in or on the probe in a known special relation to the exposure area, and obtaining an image of the probe and at least a portion of the exposure area with the markers being visible in the image, and using the markers that are visible in the image to position the probe and thus to also position the exposure area.

The above-discussed advantages that are achieved by the device in accordance with the present invention are also achieved by the method in accordance with the present invention.

In an embodiment of the method, an optical image of a subject region containing at least one part of the exposure area is generated in which optical image the exposure area is indicated, in particular in that a luminophore is applied that preferably accumulates in a tumor. The exposure area can then be correctly positioned in a particularly simple and graphic manner in that the exposure area is brought into congruence with the area marked by the luminophore.

In a further preferred embodiment of the invention, an ultrasound marker is applied which is a substance that preferably accumulates in a tumor and is accompanied by gas bubbles or generates these. These gas bubbles are particularly clearly shown in an ultrasound image.

A method according to the invention is in particular suitable to assist the treatment of a prostate, bladder or kidney tumor in which the probe is inserted into a urethra or a ureter.

DESCRIPTION OF THE PREFERRED EMBODIMENTS

Figure 1:
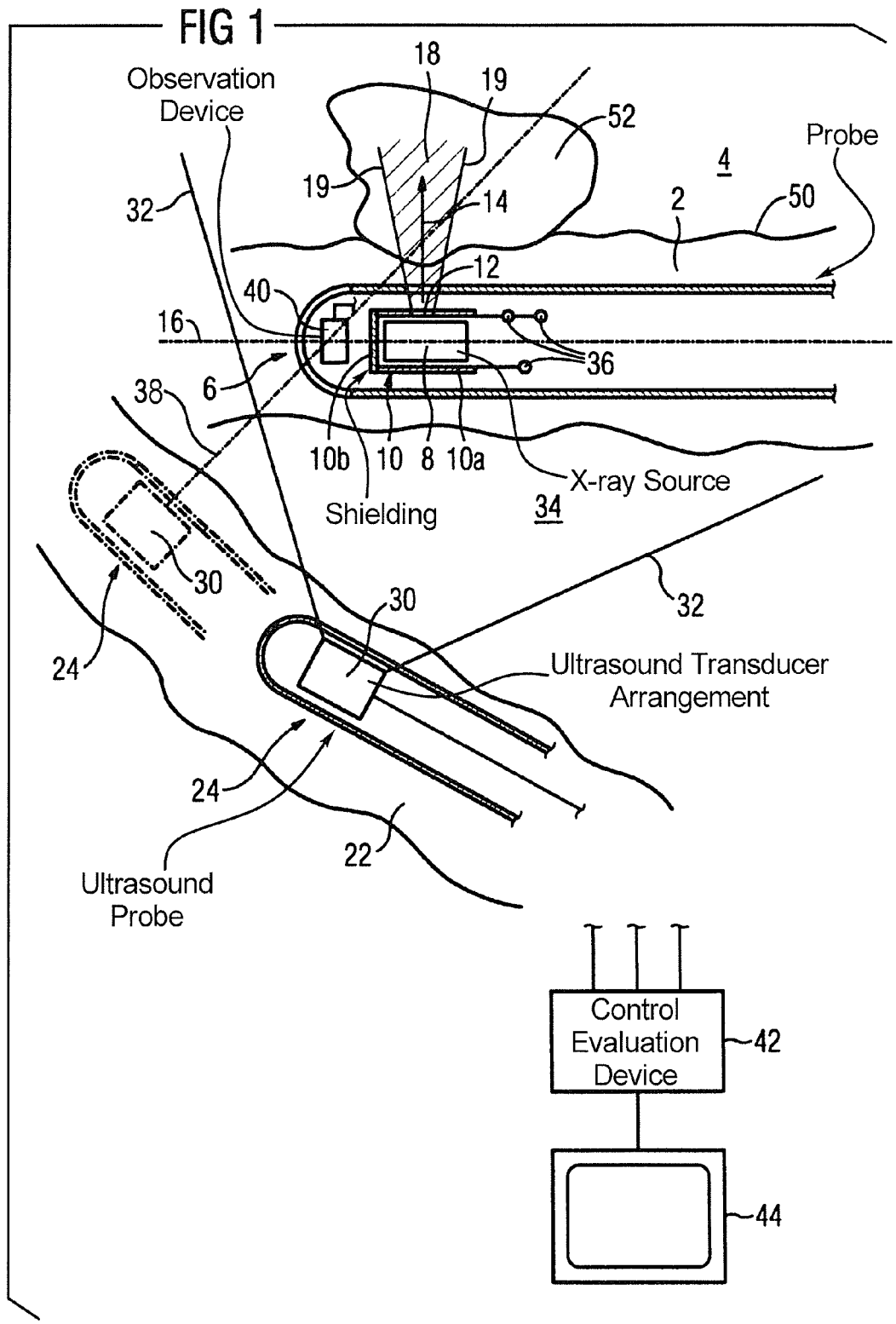
FIG. 1 schematically illustrates an embodiment of an x-ray brachytherapy system constructed and operating in accordance with the present invention.

According to FIG. 1, a probe 6 (a catheter in the example) in which an x-ray source 8 is arranged at its distal end is inserted into a cavity (lumen) 2 of a body 4 (which is, for example, a urethra). A shielding 10 is associated with the x-ray source 8, which shielding 10 in the exemplary embodiment contains a cylindrical part 10a that is provided in its circumference with a diaphragm or aperture 12 through which x-rays 14 can exit perpendicular to the longitudinal axis 16 of the probe 6, i.e. radially in a (for example conical) exposure area 18 defined by the shape of the aperture 12 and its distance from the anode of the x-ray source 8, which exposure area 18 is emphasized by hatching in FIG. 1 and is indicated by boundary lines 19.

The cylindrical part 10a of the shielding 10 is arranged within the probe 6 such that it can be rotated around its longitudinal axis 16 so that the exposure area 18 can likewise be pivoted on this longitudinal axis 16. The outer wall of the probe 6 advantageously is formed of a polymer material, such that it is at least semi-permeable to ultrasound.

The shielding 10 possesses on its front side a front plate 10b that is provided with a closable diaphragm (not shown in detail in the Figure) with which it is possible to selectively radiate x-rays 14 in the direction of the longitudinal axis 16. In this case either a movable lock is provided with which the aperture 12 can be closed or an additional shielding is provided that is arranged in the probe 6 such that the aperture 12 can be positioned in the region of this shielding.

An ultrasound probe 24 generating an ultrasound image is inserted as an imaging device into an additional cavity 22 of the body 4 located in proximity to the cavity 2 (for example the rectum), in which ultrasound probe 24 is arranged at its distal end an ultrasound transducer arrangement 30 that generates an ultrasound image from a flat subject area 34 (illustrated by boundary lines 32) that overlays at least a portion of the exposure area 18. The ultrasound transducer arrangement 30 is a linear transducer array or two linear transducer arrays that generate ultrasound images in slice planes perpendicular to one another (in the example parallel and perpendicular to the plane of the drawing). Probes of this type are known in ultrasound diagnostics as biplanar rectal probes.

Moreover, in FIG. 1 the ultrasound probe 24 is shown in a position (marked by dashes) in which it generates an ultrasound image in a subject plane perpendicular to the plane of the drawing which intersects the plane of the drawing in an intersection line 38 marked by dashes.

Moreover, the probe 6 contains a schematically indicated optical observation device 40 with which a subject region can be observed that renders at least a portion of the exposure area 18.

A number of markers 36 (of which only three are shown in FIG. 1) are arranged in the probe 6. These markers 36 (for example spheres or gas-filled (air) cavities with approximately 1 mm diameter) are detectable in the ultrasound image generated by the ultrasound transducer arrangement 30 and enable a reconstruction of the intersection surface of the exposure area 18 with the subject plane detected by the ultrasound transducer arrangement 30. In the example the markers 36 are rigidly coupled on the rotatable cylindrical part 10a of the shielding and are located in a stationary relation to the exposure area 18. For example, the markers simultaneously have an increasing angle position and an increasing distance relative to a presentable geometric point (for example the proximal edge of the cylindrical part 10a). The angle position can then be concluded from the distance of a marker 36 from the edge. All markers 36 are located at a point of the probe 6 that can be shown in an ultrasound image or that is transparent to ultrasound. In the example illustrated in the Figure, markers 36 are shown that are located in a plane that contains the center axis of the bundle of x-rays 14. If these three markers 36 are detected in an ultrasound image, this is an indication that the imaged subject plane likewise contains this center axis. The position of the exposure area 18 can now be concluded from the position of the three markers 36 in the ultrasound image.

In an embodiment the markers 36 can also be depicted in an x-ray image, such that position and angle position of the probe 6 can also be monitored with an x-ray apparatus.

The probe 6 and the ultrasound probe 24 are connected to a control and evaluation device 42 with which the x-ray source 8, the ultrasound transducer arrangement 30 and the observation device 40 are controlled and the signals transmitted from the ultrasound transducer arrangement 30 and from the observation device 40 are evaluated so that they can be presented as an ultrasound image or as an optical image on a display device 44 (for example a monitor). With the aid of the control and evaluation device 42, the markers 36 can also be identified and the exposure area 18 can be reconstructed with accurate position and identified in the ultrasound image.

In the example of FIG. 1 a tissue zone 52 to be therapeutically treated (in the example a prostate tumor that should be irradiated with x-rays 14) is located in the region of the wall 50 of the cavity 2. The tissue zone 52 to be treated can also be a different tumor accessible via a body opening, for example a bladder tumor or a kidney tumor.

Figure 2:
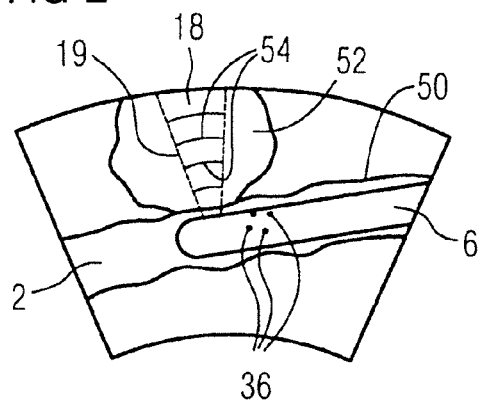
FIGS. 2 and 3 respectively show ultrasound images obtained in planes that are perpendicular to each other and intersect each other, with the exposure area being mixed into the respective images of the intersection planes.

This tissue zone 52 as well as the wall 50 are schematically depicted in the ultrasound image of FIG. 2. In this ultrasound image the intersection surface of the exposure area 18 with the subject plane detected by the ultrasound transducer arrangement is, for example, identified by rendering its lateral boundary lines 19. The exposure area 18 mixed into the ultrasound image in this manner enables a correct positioning of the probe or, respectively, of the x-ray source.

Three markers 36 with which a reconstruction of the position of the exposure area 18 is possible are apparent in the ultrasound image. In the example all three markers 36 are located in the image plane. In this case the center axis of the x-ray bundle lies in the subject plane (intersection plane) rendered in the ultrasound image and the cavity 2 and the probe 6 are shown in the idealized arrangement (shown in FIG. 1) in the form of a longitudinal section.

Moreover, lines 54 of equal dose rating that indicate the current local dose rating to the therapist are mixed into the ultrasound image, for instance. These lines 54 are located, for example, among one another at an interval that corresponds to the decrease of the dose rating to 1/e, respectively. These are approximately 1.2 cm given an x-ray radiator with an average energy of 20 keV in the tissue. The therapist can then adjust the required dose rating by changing the operating parameters of the x-ray source (anode current, acceleration voltage). These lines 54 of the same dose rating then shift in the ultrasound image corresponding to the dose rating changing with the variation of the operating parameters.

The use of an ultrasound marker is also possible. A substance that preferably accumulates in the tumor and is simultaneously accompanied by, for example, small gas bubbles or that generates small gas bubbles is administered to the patient. These gas bubbles are particularly clearly shown in the ultrasound image.

As explained in the preceding, in the shown example the center axis of the x-ray beam lies in the subject plane (intersection plane) rendered in the ultrasound image, such that the lines 54 have a circular arc-shaped form.

Figure 3:
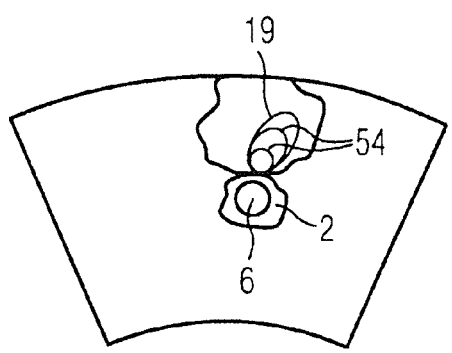

In the example of FIG. 3 an ultrasound image is shown as it can arise when the ultrasound probe 24 is located in a position marked by dashes in FIG. 1 and the subject plane runs perpendicular to the plane of the drawing of FIG. 1 and at an angle relative to the center axis of the probe 6, as this is illustrated using the intersection line 38 (marked by dashes in FIG. 1) between subject plane and plane of the drawing. In this case the cavity 2 and the probe 6 are visible in the form of a cross-section running at an angle. Like the lines 54 of equal dose rating, the boundary line 19 of the x-ray then has an approximately elliptical shape. If the intersection plane is oriented perpendicular to the center axis of the x-rays, the boundary lines 19 and the line 54 exhibit a circular shape.

Figure 4:
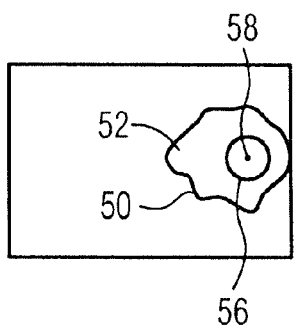
FIG. 4 schematically illustrates an optical image obtained in the environment of the probe of the brachytherapy system in accordance with the present invention, wherein pathological tissue in the environment has been made visible by a luminophore carried by the probe.

According to FIG. 4, an optical image, in which the wall 50 of the cavity is visible given corresponding illumination, is generated from the surroundings of the probe. A luminophore can be additionally applied (for example directly with the aid of the probe) preferentially accumulates in the tissue zone 52 if this is a tumor and that, for example, is excited by the light source used for illumination and emits fluorescence light in the visible range, so the tumor 52 can also be made visible in the optical image at least in its surface region with which it borders the cavity. If the envelope of the x-ray beam striking the surface of the wall 50 is additionally mixed in as a circular line 56 and its center axis is mixed in as a point 58, the exact positioning can also be effected with the aid of the optical image in addition to the positioning with the ultrasound image since in this case image information exists from a different plane, for example a plane perpendicular to the image plane of the ultrasound image.

Figure 5:
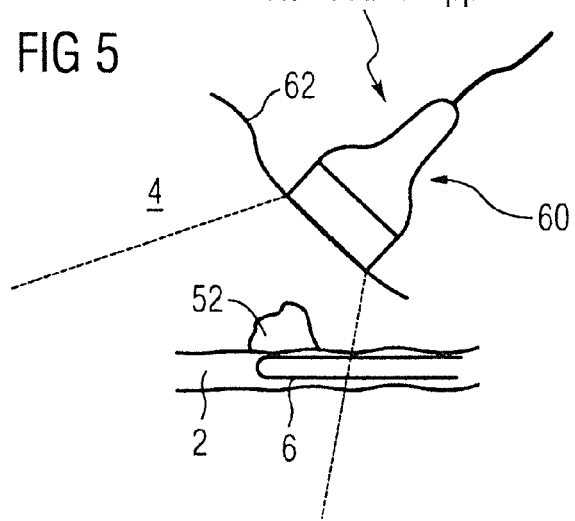
FIG. 5 schematically illustrates a further embodiment of the x-ray brachytherapy system in accordance with the present invention, using an extracorporeal ultrasound applicator as the imaging device.

In the exemplary embodiment according to FIG. 5, instead of an ultrasound probe that can be inserted into the inside of the body 5 an ultrasound head 60 is provided as an ultrasound applicator, which ultrasound head 60 is attached on the outer surface 62 of the body 4 and detects the probe 6 and the tissue zone 52 starting from this surface 62 of the cavity 2.

The invention is presented using a catheter inserted into the cavity of a body. In principle the invention is also suitable for probes that are directly inserted into the tissue, as this is the case in the invasive post-treatment (explained above) of a tumor bed of a previously removed tumor. The tissue zone to be treated can also be a vessel wall that should be irradiated after the implementation of a dilatation to reduce the restenosis rate.

Although modifications and changes may be suggested by those skilled in the art, it is the intention of the inventors to embody within the patent warranted heron all changes and modifications as reasonably and properly come within the scope of their contribution to the art.

We claim as our invention:

1. An x-ray brachytherapy system comprising:
   a probe configured for insertion into a body of a living subject, said probe having a distal end;
   an x-ray source located in said probe at said distal end, said x-ray source radiating x-rays in an x-ray beam into an exposure area outside of the probe in the body of the living subject, said exposure area being defined by an extent of said x-ray beam;
   a plurality of markers located in or on said probe in a known spatial relation to the exposure area;
   an image device that has no mechanical connection to and is positionable at an image device position relative to said body independently of a probe positon said probe in said body, that generates an image of at least a portion of said exposure area, with no mechanical constraint being imposed on said image device position by said probe position;
   said plurality of markers located in or on said probe being comprised of material that makes said markers visible in said image; and
   a control and evaluation device having an associated display device, said control and evaluation device being supplied with said image and being configured to determine a correct position of said at least said portion of said exposure area in said image by evaluating respective positions of said markers in said image in relation to said exposure area, and to cause said at least said portion of said exposure area, in said correct position, and said markers, to be mixed into said image at said display.

2. A system as claimed in claim 1 comprising a shielding in said probe that is movable relative to said x-ray source to adjust a position or size of said exposure area.

3. A system as claimed in claim 1 wherein said imaging device mixes lines indicating equal x-ray dose rating into at least said portion of said exposure area displayed in said image at said display device.

4. A system as claimed in claim 1 wherein said imaging device displays an indication of the position of the x-ray source in the image at said display device.

5. A system as claimed in claim 1 wherein said imaging device is an ultrasound applicator.

6. A system as claimed in claim 5 wherein said ultrasound applicator is an ultrasound probe configured for insertion into a body cavity of said subject.

7. A system as claimed in claim 6 wherein said ultrasound applicator comprises an ultrasound transducer arrangement that generates ultrasound images respectively in two intersecting planes that are perpendicular to each other.

8. A system as claimed in claim 5 wherein said ultrasound applicator is an extracorporeal ultrasound applicator.

9. A system as claimed in claim 1 wherein said probe has a proximal end and a longitudinal axis proceeding from said proximal end to said distal end, and wherein said image device comprises a device housing having a distal end and a proximal end and a longitudinal, axis between said distal end and said proximal end of said device housing, and an imaging field source located in said device housing at said proximal end thereof, and wherein said image device and said probe are respectively positionable at an image device position and a probe position at which said longitudinal axis of said probe and said longitudinal axis of said image device are not parallel with each other.

10. A method for positioning an x-ray brachytherapy probe in an interior of a body of a living subject, comprising the steps of:
 inserting an x-ray brachytherapy probe into the body of a living subject and carrying within said probe, at a distal end of the probe, an x-ray source;
 radiating x-rays in an x-ray beam from said x-ray source into an exposure area in the body of the living subject outside of the probe for x-ray brachytherapy, said exposure area being defined by an extent of said x-ray beam;
 arranging a plurality of markers in or on the probe in a known special relation to the exposure area;
 positioning an imaging device, having no mechanical connection to said probe, at an imaging device position relative to said body separately and independently of a probe position said probe in said body, with no mechanical constraint being imposed on said image device position by said probe position,
 with said imaging device, generating an image of at least a portion of said exposure area, said markers being comprised of a material that makes said markers visible in said image together with said exposure area;
 in a control and evaluation device having an associated display device, determining a correct position of said at least said portion of said exposure area in said image by evaluating respective positions of said markers in said image in relation to said exposure area; and
 at said display device, displaying the image and controlling positioning of said at least said portion of the exposure area in the body of the subject dependent on identification of the markers in the displayed image with said markers and said at least said portion of the exposure area mixed in the displayed image at respectively correct positions.

11. A method as claimed in claim 10 comprising controlling positioning of said exposure area by adjusting a shielding in the probe that is movable in the probe relative to the x-ray source.

12. A method as claimed in claim 10 comprising providing an identification in the displayed image of said exposure area.

13. A method as claimed in claim 12 comprising mixing lines of equal dose rating into the exposure area shown in the displayed image.

14. A method as claimed in claim 12 comprising indicating a position of the x-ray source in the displayed image.

15. A method as claimed, in claim 10 comprising generating said image as an ultrasound image.

16. A method as claimed in claim 15 comprising inserting an ultrasound applicator into a cavity of the body and generating said ultrasound image with said ultrasound applicator in said cavity.

17. A method as claimed in claim 16 comprising generating respective ultrasound images in two intersecting planes that are perpendicular to each other.

18. A method as claimed in claim 15 comprising generating said image with an extracorporeally applied ultrasound applicator.

19. A method as claimed in claim 10 comprising generating an optical image of an environment of the probe in the body of the subject that includes at least a portion of said exposure area.

20. A method as claimed in claim 19 comprising with said probe, exposing tissue in said environment of said probe to a luminophore that preferentially accumulates in tumorous tissue to make said tumorous tissue visible in said optical image.

21. A method as claimed in claim 10 comprising generating said image as an ultrasound image, and administering a substance to tissue in an environment of said probe that preferentially accumulates in tumorous tissue and that has gas bubbles associated therewith that are visible in the ultrasound image to make said tumorous tissue visible in the ultrasound image.

22. A method as claimed in claim 10 comprising inserting said probe into a urethra or a ureter of the subject.

23. A method as claimed in claim 10 comprising inserting said imaging device into the subject rectally.

24. A method as claimed in claim 10 wherein said probe has a proximal end and a longitudinal axis proceeding from said proximal end to said distal. end, and wherein said image device comprises a device housing having a distal end and a proximal end and a longitudinal axis between said distal end and said proximal end of said device housing, and an imaging field source located in said device housing at said proximal end thereof, and comprising respectively positioning said image device and said probe at an image device position and a probe position at which said longitudinal axis of said probe and said longitudinal axis of said image device are not parallel with each other.

* * * * *